US006657089B1

(12) United States Patent
Nagasawa et al.

(10) Patent No.: US 6,657,089 B1
(45) Date of Patent: Dec. 2, 2003

(54) PALLADIUM CATALYST AND PROCESS FOR PRODUCING ETHER

(75) Inventors: Atsushi Nagasawa, Wakayama (JP); Munehisa Okutsu, Wakayama (JP); Tomohito Kitsuki, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 10/111,920

(22) PCT Filed: Jul. 19, 2000

(86) PCT No.: PCT/JP00/04844

§ 371 (c)(1),
(2), (4) Date: May 1, 2002

(87) PCT Pub. No.: WO01/32306

PCT Pub. Date: May 10, 2001

(30) Foreign Application Priority Data

Nov. 2, 1999 (JP) .............................. 11/312092
Jun. 7, 2000 (JP) ....................... 2000-170516

(51) Int. Cl.⁷ .............................................. C07C 41/01
(52) U.S. Cl. ..................... 568/680; 568/599; 568/664; 568/670
(58) Field of Search ................ 568/599, 664, 568/670, 680; 502/200, 262, 439; 423/328.1

(56) References Cited

U.S. PATENT DOCUMENTS 3,617,521 A  *  11/1971  Houston et al. ............ 208/138
4,795,732 A  *  1/1989  Barri ........................... 502/223
5,215,737 A  *  6/1993  Chu et al. .................... 423/706
5,595,715 A  *  1/1997  Roth ........................ 423/328.1
5,780,687 A  *  7/1998  Holderich et al. .......... 568/678

FOREIGN PATENT DOCUMENTS

| JP | 54-135714  | 10/1979 |
| JP | 08-509999  | 10/1996 |
| JP | 09-241185  | 9/1997  |
| JP | 3086881    | 7/2000  |

OTHER PUBLICATIONS

Ernest L. Eliel et al.: "Reduction with metal hydrides. XII. Reduction of acetals and ketals with lithium aluminum hydride–aluminum chloride" J. Amer. Chem. Soc., vol. 84, pp. 2371–2377 Jan. 3, 1962.

* cited by examiner

*Primary Examiner*—Rosalynd Keys
(74) *Attorney, Agent, or Firm*—Oblon, Spivak, McClelland, Maier & Neustadt, P.C.

(57) ABSTRACT

This invention relates to a palladium catalyst comprising a mesoporous aluminosilicate which has been treated with ammonia or a salt thereof, and palladium supported on said mesoporous aluminosilicate; and also to a process for producing an ether, which comprises reacting a cyclic acetal and hydrogen in the presence of the palladium catalyst.

5 Claims, No Drawings

PALLADIUM CATALYST AND PROCESS FOR PRODUCING ETHER

TECHNICAL FIELD

This invention relates to palladium catalysts useful in the production of hydroxyethers which are useful as oil stain removers, water-soluble organic solvents, polar oils, emulsifiers, lubricants, humectants or the like, or as intermediates for producing surf actants, and also to a process for producing hydroxyethers by use of the palladium catalysts.

BACKGROUND ART

Known as hydrogenolytic processes for acetal compounds are (1) a process which uses a mixture of an alkylaluminum halide compound or an aluminum halide and lithium aluminum hydride [E. L. ELIEL et al., J. Am. Chem. Soc., 84,2371 (1962)] and (2) a process which uses a hydrogenation catalyst comprising a metal such as palladium, platinum or rhodium supported thereon in a hydrogen atmosphere (JP-A-54-135714).

However, the process (1) involves a problem in safety because the reagents to be used therein have considerable inflammability and are required in stoichiometric amounts. Thus the process is also accompanied by a problem in that a large amounts of wastes are produced. The process (2), on the other hand, is free of such problems and is advantageous. However, in the case where the acetal compound is an acetal of a polyhydric alcohol such as a cyclic acetal, the process involves a problem in that the resulting product inevitably has a mixed composition of monoethers, diethers and the like through transacetalization (or acetal exchange) or the like.

An object of the present invention is to provide a catalyst capable of obtaining a monoether with high selectivity in the synthesis of an ether and also a process for synthesizing a monoether with high selectivity through hydrogenolysis of a cyclic acetal by using the catalyst.

DISCLOSURE OF THE INVENTION

The present inventors have found that the above-described problems can be solved by using a catalyst comprising palladium supported on a mesoporous aluminosilicate which is a porous carrier having a substantially uniform pore size greater than that of zeolite. The inventors have also found that a catalyst especially excellent in activity in the production of an ether can be provided by supporting palladium on a mesoporous aluminosilicate treated beforehand with ammonia or a salt thereof.

Specifically, the present invention provides a process for producing an ether, which comprises reacting a cyclic acetal and hydrogen in the presence of a palladium catalyst supported on a mesoporous aluminosilicate The present invention also provides a palladium catalyst comprising palladium supported on a mesoporous aluminosilicate which has been treated with ammonia or a salt thereof.

BEST MODES FOR CARRYING OUT THE INVENTION

The term "mesoporous aluminosilicate" as used herein, which is a carrier in the palladium catalyst according to the present invention, means an aluminosilicate having a uniform pore size of from 2 to 50 nm. This uniform pore size can be determined by a powder X-ray diffraction pattern, and is preferably from 2 to 10 nm, particularly from 2 to 6 nm. A monoether can be obtained with high selectivity in the present invention because transacetalization is controlled inside of such mesoporous pores. Therefore, the best results can be obtained by using a catalyst having a pore size and a palladium dispersion state which are suitable for substrates.

The palladium catalyst according to the present invention can be produced by synthesizing a mesoporous aluminosilicate having a pore size greater than that of zeolite and then having palladium supported on the mesoporous aluminosilicate.

The mesoporous aluminosilicate can be synthesized, for example, by the process disclosed in Bull. Chem. Soc. Jpn., 63, 988 (1990). From the standpoint of synthesis, however, the percentage of Al based on Si is preferably 10 wt. % or lower, and the pore size of the mesoporous aluminosilicate is preferably 2 to 10 nm, especially at 2 to 6 nm.

In the present invention, it is preferred to have palladium supported on a mesoporous aluminosilicate after treating the mesoporous aluminosilicate with ammonia or a salt thereof.

As a method for treating a mesoporous aluminosilicate with ammonia or its salt in advance, it is preferred to subject a synthesized mesoporous aluminosilicate to neutralization or ion exchange with ammonia or its salt. In this method, ammonia may be used in the form of either gas or an aqueous solution. Examples of the salt of ammonia can include ammonium salts of inorganic acids such as ammonium chloride, ammonium sulfate and ammonium carbonate; and ammonium salts of lower organic acids (carbon number: 1 to 3) such as ammonium acetate, ammonium formate and ammonium chloride, with ammonium chloride being particularly preferred. The ammonia salt for use in this treatment can be used in the form of an aqueous solution. It is necessary to use ammonia or its salt in an amount sufficiently greater than that of contaminated sodium ions. Specifically, a mesoporous aluminosilicate may be dispersed at 0 to 100° C., preferably at room temperature to 80° C. in an aqueous solution of ammonia or its salt in a sufficiently excess amount such as 1 to 100 molar times, preferably 1 to 50 molar times as much as the molar amount of aluminum in the mesoporous aluminosilicate to bring the mesoporous aluminosilicate into contact with the solution of ammonia or its salt, followed by rinse. Before palladium is supported, the thus-treated mesoporous aluminosilicate may be calcined at 200 to 700° C., preferably at 300 to 600° C., or may be used without calcination for supporting palladium. By treating the mesoporous aluminosilicate with ammonia or its salt as described above before palladium is supported thereon, the amount of sodium ions contaminated in the mesoporous aluminosilicate can be significantly decreased, leading to an improvement in the palladium supporting efficiency through ion exchange and also to a significant improvement in the catalytic reaction activity of the supported palladium. When employed especially in synthesizing an ether from a polyhydric alcohol and a carbonyl compound, the reaction activity and selectivity to the monoether formation are improved significantly.

Processes for supporting palladium on the mesoporous aluminosilicate include, for example, impregnation process, ion exchange process, and CVD process. In general, impregnation process is used widely. As a process for having palladium supported on the mesoporous aluminosilicate, however, ion exchange process is preferred.

The process in which palladium is supported by ion exchange is suitable for the catalyst preparation process according to the present invention, because this process makes it possible to have palladium supported rather readily in a highly dispersed state.

Examples of palladium salts usable in this supporting process include $PdCl_2$, $Pd(OAc)_2$, $Pd(NH_4)Cl_2$, and $[Pd(NH_3)_4]Cl_2$, with $PdCl_2$ and $Pd(OAc)_2$ being particularly preferred. An ion exchange process using $PdCl_2$, $Pd(OAc)_2$ or the like includes, for example, a process in which $PdCl_2$ is dissolved in aqueous ammonia or $Pd(OAc)_2$ is dissolved in a liquid mixture of acetone and water, and a mesoporous aluminosilicate or a salt thereof is dispersed in the resultant solution to bring the mesoporous aluminosilicate or its salt into contact with the solution. A process using a solution of $PdCl_2$ in aqueous ammonia is preferred. No particular limitation is imposed on the amount of $PdCl_2$ or the treatment temperature, but the amount of $PdCl_2$ is preferably from 0.01 to 500 wt. %, more preferably from 0.1 to 200 wt. % based on the amount of mesoporous silicate, and the treatment temperature is preferably from 0 to 100° C., more preferably from room temperature to 80° C.

The amount of palladium supported on the mesoporous aluminosilicate is preferably from 0.1 to 10 wt. % of the whole amount of the catalyst. The amount greater than this range has a higher possibility of giving an adverse effect such as sintering when palladium is supported.

Subsequent to supporting of palladium on the mesoporous aluminosilicate, it is preferred to conduct calcination at 200 to 700° C., particularly at 300 to 600° C.

The palladium catalyst thus prepared is used as a catalyst, for example, for producing an ether by reacting a cyclic acetal with hydrogen as illustrated by the following reaction sheme.

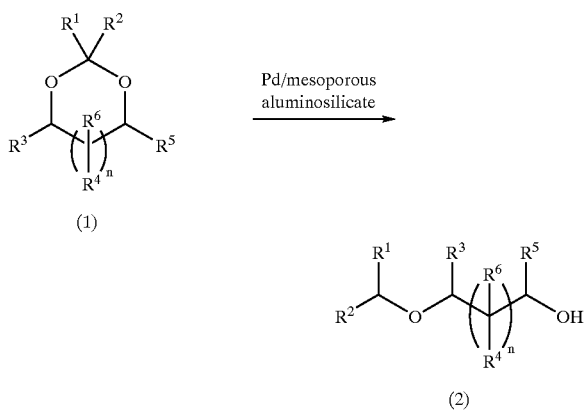

wherein $R^1$ and $R^2$ may be the same or different and represent a hydrogen atom or a linear or branched hydrocarbon group having 1 to 18 carbon atoms, $R^3$ to $R^6$ may be the same or different and represent a hydrogen atom, a hydroxyl group, or a substituted or unsubstituted, linear or branched hydrocarbon group or hydroxyalkyl group having 1 to 14 carbon atoms, and n denotes a number of from 0 to 2, with a proviso that $R^1$ and $R^2$ do not represent hydrogen atoms at the same time, and each of $R^1$ and $R^2$, $R^3$ and $R^4$, and $R^3$ and $R^5$, together with the adjacent carbon atoms, may form a cyclic structure.

In the cyclic acetal used in the present invention, preferred examples of $R^1$ and $R^2$ in the formula (1) include hydrogen atom; alkyl groups having 1 to 12 carbon atoms, such as methyl, ethyl, propyl, isopropyl, butyl, isobutyl, pentyl, hexyl, heptyl, isooctyl and undecyl; and cyclic structures formed by $R^1$ and $R^2$, such as cyclopentane and cyclohexane.

Preferred examples of $R^3$ to $R^6$ in the formula (1) include hydrogen atom; hydroxyl group; alkyl groups having 1 to 4 carbon atoms, such as methyl, ethyl and propyl, and hydroxyl-substituted groups of these alkyl groups; and cyclic structures formed by $R^3$ and $R^4$ or $R^3$ and $R^5$, such as cyclopentane and cyclohexane. No particular limitation is imposed on the substituents of these hydrocarbon groups or hydroxyalkyl groups insofar as they are functional groups not preventing hydrogenolysis. Examples of such substituents are halogen atoms and oxo group. Preferably n is 0 or 1. Examples of the most preferred combination of $R^3$ to $R^6$ and n include $R^3$=H, $R^5$=hydroxymethyl, and n=0; and $R^3$=$R^5$=H, n=1, $R^4$=H, and $R^6$=OH.

The cyclic acetal (1) can be synthesized by acetalization (acetal formation) reaction from the corresponding carbonyl compound and polyhydric alcohol according to a conventional method.

Examples of the carbonyl compound are preferably linear, branched or cyclic compounds having 2 to 37 carbon atoms and containing one carbonyl group; more preferably aliphatic aldehydes having 2 to 19 carbon atoms and containing one carbonyl group, linear or branched ketones having 3 to 37 carbon atoms, and cyclic ketones having 5 to 8 carbon atoms; still more preferably aliphatic aldehydes having 2 to 12 carbon atoms and containing one carbonyl group, linear or branched ketones having 3 to 10 carbon atoms, and cyclic ketones having 5 to 6 carbon atoms. Of these, particularly preferred are propylaldehyde, butylaldehyde, isobutylaldehyde, valeric aldehyde, isovaleric aldehyde, hexylaldehyde, heptylaldehyde, octylaldehyde, isononylaldehyde, dodecylaldehyde, acetone, methyl ethyl ketone, methyl isobutyl ketone, and cyclohexanone. In the present invention, one of more of these carbonyl compounds can be used.

Illustratives of the polyhydric alcohol are ethylene glycol, 1,2- or 1,3-propanediol, glycerin, 1,2-, 1,3- or 2,3-butanediol, 1,2- or 2,4-pentanediol, trimethylolethane, trimethylolpropane, xylitol, arabitol, 1,2- or 1,3-cyclopentanediol, 1,2- or 1,3-cyclohexanediol, and 2,3-norbornanediol, and are preferably glycerin and ethylene, particularly glycerin.

The ratio (molar ratio) of the polyhydric alcohol to the carbonyl compound used in the acetalization reaction ranges from 1.5 to 0.2, especially from 1.2 to 0.6. This reaction can be conducted using as an acid catalyst paratoluenesulfonic acid, methanesulfonic acid, sulfuric acid or the like in an amount of from 0.01 to 5 mol %, preferably from 0.1 to 1 mol % based on the carbonyl compound.

The above-described acetalization reaction is conducted preferably in the absence of solvent, or in an inert solvent such as xylene, toluene, benzene, octane, isooctane, heptane, hexane, cyclohexane, pentane, butane, ligroin or petroleumether, or in a mixed solvent thereof, while removing water produced in the process. Further, the acetalization reaction can be conducted under a nitrogen gas stream, in a nitrogen atmosphere or in an air atmosphere. The reaction temperature varies depending upon the boiling point of the carbonyl compound to be used, but from the viewpoint of sufficient reaction velocity and suppressing coloration and side reactions, the reaction temperature is preferably from 20 to 130° C., particularly from 50 to 100° C. The reaction time varies depending upon various conditions, but in general, is preferably from 1 to 30 hours. After the cyclic acetal thus obtained is neutralized and subjected to pretreatment such as filtration and washing, it can be purified by procedure such as clay treatment, crystallization or distillation.

In the hydrogenolytic reaction of the cyclic acetal obtained as described above, the present invention uses as a catalyst the palladium catalyst supported on the mesoporous aluminosilicate.

The amount of the palladium catalyst to be used in the present invention varies depending on the amount of supported palladium. For example, in the case of a palladium catalyst comprising 5 wt. % of palladium, the palladium catalyst may be used in an amount of from 0.1 to 10 wt. % based on the hydroxy compound to be used.

When reacting the cyclic acetal compound in the presence of the above-described catalyst in a hydrogen atmosphere, no particular limitation is imposed on the hydrogen pressure. The reaction may be conducted either under an elevated pressure or atmospheric pressure, but a range of from 0.1 (atmospheric pressure) to 29.4 MPa is preferred, with a range of from 0.1 (atmospheric pressure) to 19.6 MPa being particularly preferred. The reaction system can be either a closed system or a hydrogen stream system.

No particular limitation is imposed on the reaction temperature, but a range of from 10 to 220° C., especially a range of from 30 to 200° C. is preferred. An appropriate reaction time can be chosen depending upon the reaction temperature, the hydrogen pressure, the catalyst amount, etc., but in general, the reaction time ranges from 1 to 40 hours, preferably from 1 to 20 hours. In the reaction of the present invention, a solvent can be used. Examples of such solvents are hydrocarbon solvents such as hexane, heptane and octane. The solvent is preferably used in an amount 0.5 to 2 times by volume as much as the reaction mixture. Further, the carbonyl compound or polyhydric alcohol, the raw materials of the cyclic acetal, maybe added to the reaction system. In addition, an acidic substance such as phosphoric acid and/or a halide of a Group III element of the periodic table may also be added in trace amounts.

In this reaction, transacetalization is so controlled that the monoether can be obtained with high selectivity. Depending upon differences in the cut position of the cyclic acetal (between the 1-position and the 2-position, or between the 2-position and the 3-position), two types of monoethers can be obtained. Both of them are useful as oil stain removers, water-soluble organic solvents, polar solvents, emulsifiers, lubricants, humectants and the like and also as intermediates for producing surfactants, and can be used in these applications either after isolation or as a mixture thereof.

Purification of the monoether from the reaction mixture can be conducted by a method known per se in the art, for example, by a method such as distilling-off of the solvent, washing, recrystallization, distillation, chromatography or a combination thereof after conducting filtration to remove the catalyst.

The amounts of palladium, silicon and aluminum contained in the palladium catalyst according to the present invention can be determined by an elemental analysis such as atomic absorption spectrometry, while the amount of sodium contained in the palladium catalyst according to the present invention can be determined by X-ray electron spectrometry.

EXAMPLES

Example 1

Preparation of Palladium Catalyst (1)

(1) Synthesis of a Mesoporous Aluminosilicate

Water glass (250 g), sodium aluminate (10.8 g) and water (550 mL) were charged in a 1-L stainless steel beaker. After they were stirred at 70° C. for 3 hours, water was evaporated. Subsequent to further drying, the mixture was calcined at 700° C. for 5 hours to obtain a laminated aluminosilicate (120 g).

To the thus-obtained laminated aluminosilicate (Si:Al weight ratio=95:5; 15 g), water (100 mL) was added. Subsequent to stirring, cetyldimethylammonium chloride (12 g), 1,3,5-trimethylbenzene (5.0 g) and water (300 mL) were added. After the resulting mixture was stirred at 70° C. for 3 hours, the mixture was stirred for 12 hours while controlling its pH at 8.5 with $2 \times 10^{-3}$ mol/m$^3$ hydrochloric acid. The mixture was allowed to cool down to room temperature, followed by filtration to collect solid matter. The solid matter was washed with water, dried, and then calcined at 550° C. for 8 hours to obtain a mesoporous aluminosilicate. Further, $2 \times 10^{-3}$ mol/m$^3$ aqueous solution of ammonium chloride (200 mL) was added. The thus-prepared mixture was stirred at 50° C. for 3 hours, followed by filtration to collect solid matter. The solid matter was washed with water, dried, and then calcined at 500° C. for 2 hours to obtain a white solid (14 g). By an XRD analysis, its pore size was found to be 4.7 nm.

(2) Supporting of Palladium on the Mesoporous Aluminosilicate

Palladium chloride (2.0 g) was dissolved in 28% aqueous ammonia (250 mL) and water (750 mL), and the resulting mixture was heated to 50° C. The mesoporous aluminosilicate (5.0 g), which had been synthesized and treated in the synthesis (1), and water (50 mL) were added, followed by stirring for 3 hours. The mixture thus prepared was filtered to collect solid matter. The solid matter was washed with water, dried, and then calcined at 500° C. for 2 hours to obtain a mesoporous aluminosilicate with palladium supported thereon [15.0 g, palladium catalyst (1)]. As a result of an elemental analysis by atomic absorption spectroscopy, the amount of palladium supported on the catalyst was found to be 2.1%. According to an analysis using of X-ray electron spectroscopy (manufactured by Shimadzu Corporation), its sodium content was found to be 0.1% or less.

Example 2

Preparation of Palladium Catalyst (2)

(1) Synthesis of a Mesoporous Aluminosilicate

To a laminated aluminosilicate (50 g) obtained in a similar manner as in Example 1, water (300 mL) was added. Subsequent to stirring, cetyldimethylarmnonium chloride (40 g) and water (1 L) were added. After the resulting mixture was stirred at 70° C. for 3 hours, the mixture was stirred for 12 hours while controlling its pH at 8.5 with $2 \times 10^{-3}$ mol/m$^3$ hydrochloric acid. The mixture was allowed to cool down to room temperature, followed by filtration to collect solid matter. The solid matter was washed with water, dried, and then calcined at 700° C. for 7 hours to obtain a mesoporous aluminosilicate. Further, $2 \times 10^{-3}$ mol/m$^3$ aqueous solution of ammonium chloride (800 mL) was added. The mixture thus prepared was stirred at 50° C. for 3 hours, followed by filtration to collect solid matter. The solid matter was washed with water, dried, and then calcined at 500° C. for 2 hours to obtain a white solid (38 g). As a result of an elemental analysis by atomic absorption spectrometry, the Al:Si ratio was found to be 4.8:95.2 by weight. Further, its pore size was found to be 3.5 nm according to an XRD analysis, and its specific surface area as determined by the BFT method was 750 m$^2$/g.

(2) Supporting of Palladium on the Mesoporous aluminosilicate

Palladium chloride (0.5 g) was dissolved in $1 \times 10^{-3}$ mol/m$^3$ aqueous ammonia (30 mL) and water (50 mL), and the resulting mixture was heated to 50° C. The mesoporous aluminosilicate (2.0 g) synthesized and treated in the synthesis (1) was added, followed by stirring for 3 hours. The mixture thus prepared was filtered to collect solid matter. The solid matter was washed with water, dried, and then calcined at 550° C. for 2 hours to obtain a mesoporous aluminosilicate with palladium supported thereon [palladium catalyst (2)]. As a result of an elemental analysis by atomic absorption spectroscopy, the amount of palladium supported on the catalyst was found to be 6.7%. According to an analysis using an X-ray electron spectrometer, its sodium content was found to be 0.1% or less.

(3) Catalytic Effect (Production of 1,3-Dimethylbutyl Hexadecyl ether)

(a) Hexadecyl alcohol (116 g, 0.5 mol), 4-methyl-2-pentanone (100 g, 1.0 mol) and, as a catalyst, the palladium catalyst (2) (1.5 g) were charged in a 500 mL autoclave equipped with a hydrogen gas inlet tube and a stirrer, and were reacted at 150° C. for 5 hours under a hydrogen pressure of 9.8 MPa.

After completion of the reaction, the catalyst was removed by filtration, and excess 4-methyl-2-pentanone was distilled off under reduced pressure. The residue was then purified by distillation under reduced pressure to obtain the aimed 1,3-dimethylbutyl hexadecyl ether as a colorless clear oil (153 g, 0.47 mol). The isolation yield was 94%. By a gas chromatographic analysis, its purity was found to be 99.5%.

(b) A palladium catalyst comprising palladium supported thereon was prepared in a similar manner as in the preparation of the above-described palladium catalyst (2) except for the omission of the treatment of the mesoporous aluminosilicate with $2 \times 10^{-3}$ mol/m$^3$ ammonium chloride. The amount of supported palladium was 5%, while the content of sodium was 2.1%. Using the palladium catalyst, a reaction was conducted as in the above production (a). As a result, the isolation yield of 1,3-dimethylbutyl hexadecyl ether was 51%.

Example 3

Synthesis of 3-Octyloxy-1,2-propanediol (1) 2-Heptyl-4-hydroxymethyl-1,3-dioxolane and 2-Heptyl-1,3-dioxan-5-ol In a reaction vessel having a capacity of 3 L and equipped with a thermometer, a reflux condenser, a Dean-Stark trap, a calcium chloride tube and a stirrer, octyl aldehyde (512.0 g, 3.994 mol), glycerin (404.5 g, 4.392 mol), paratoluene-sulfonic acid monohydrate (3.80 g, 0.02 mol) and toluene (400 mL) were charged. The contents were heated under stirring, and at a reflux temperature, a reaction was conducted for 4 hours to distill off a stoichiometric amount of water. After completion of the reaction, sodium carbonate (4.24 g, 0.04 mol) was added for neutralization, followed by the addition of water (100 mL). The resulting mixture was then allowed to stand to separate it into layers. After the upper layer was washed twice with brine (100 mL), it was distilled to obtain a mixture of the title compounds (802.3 g). By a gas chromatographic analysis, the purity of the mixture was found to be 98.5 wt. %.

(2) 3-Octyloxy-1,2-propanediol

The mixture obtained in the production (1) (22.3 g, 0.11 mol) and the palladium catalyst (1) (2.25 g) were charged in a 70-mL autoclave, followed by a reaction under a hydrogen pressure of 7.0 MPa at 190° C. for 15 hours. After completion of the reaction, the catalyst was removed by filtration to obtain a crude product (18.0 g).

As a result of a gas chromatographic analysis, the weight ratio of monoalkyl ethers to dialkyl ethers in the crude product was found to be 94:6. In the monoalkyl ethers, 16 wt. % of 2-octyloxy-1,3-propanediol was contained in addition to the title compound.

Comparative Example 1

[Synthesis of 3-Octyloxy-1,2-propanediol Using a Commercial Catalyst]

A reaction was conducted in a similar manner as in Example 1 except that, as a catalyst, commercial 5 wt. % palladium-charcoal powder (1.1 g) was used in place of the palladium catalyst (1). The weight ratio of monoalkyl ethers to dialkyl ethers was 68:32.

Example 4

Synthesis of 3-sec-Butoxy-1,2-propanediol (1) 2-Methyl-2-ethyl-4-hydroxymethyl-1,3-dioxolane In a reaction vessel having a capacity of 3 L and equipped with a thermometer, a reflux condenser, a Dean-Stark trap, a calcium chloride tube and a stirrer, methyl ethyl ketone (400 g, 5,547 mol), glycerin (561.91 g, 6.102 mol), paratoluene-sulfonic acid monohydrate (21.10 g, 0.1109 mol) and hexane (400 mL) were charged. The contents were heated under stirring and a reaction was conducted at 67 to 74° C. for 30 hours to distill off a calculated amount of water. After completion of the reaction, the reaction mixture was cooled to 60° C., followed by the addition of sodium carbonate (23.51 g, 0.2218 mol) for neutralization. After the resulting mixture was stirred at 60° C. for 30 minutes, the temperature was gradually raised up to 120° C. to recover hexane (400 mL). Filtration was then conducted to obtain the titled product in a crude form (894.74 g). Using a Biglew tube (20 cm×1.5 cm in diameter), distillation was conducted under reduced pressure to obtain the titled compound (725.14 g, yield: 89.4%). By a gas chromatographic analysis, the purity of the compound was found to be 99.1 wt. %. b.p. 101 to 104° C./17 mmHg.

(2) 3-sec-Butoxy-1,2-propanediol

The compound obtained in the production (1) (29.2 g, 0.10 mol) and the palladium catalyst (2) (2.2 g) were charged in a 70-mL autoclave, followed by a reaction under a hydrogen pressure of 7.0MPa at 190° C. for 15 hours. After completion of the reaction, the catalyst was removed by filtration to obtain a crude product (27.2 g).

As a result of gas chromatographic analysis, the weight ratio of monoalkyl ethers to dialkyl ethers in the crude product was found to be 92:8. In the monoalkyl ethers, 15 wt. % of 2-sec-butoxy-1,3-propanediol was contained in addition to the titled compound.

Comparative Example 2

[Synthesis of 3-sec-Butoxy-1,2-propanediol by the commercial catalyst]

A reaction was conducted in a similar manner as in Example 2 except that as a catalyst, the commercial 5 wt. % palladium-charcoal powder (2.9 g) was used in place of the palladium catalyst (2). The weight ratio of monoalkyl ethers to dialkyl ethers was 70:30.

Example 5

Synthesis of 2-(1-Methylheptyloxy)ethanol

2-Hexyl-2-methyl-1,3-dioxolane (30 g, 0.17 mol), the palladium catalyst (2) (2.2 g) and phosphoric acid (110 mg) were charged in a 70-mL autoclave, followed by a reaction under a hydrogen pressure of 10 MPa at 150° C. for 5 hours. After completion of the reaction, the catalyst was removed by filtration to obtain a crude product (29.7 g).

As a result of gas chromatographic analysis, the weight ratio of monoalkyl ethers to dialkyl ethers in that crude product was found to be 88:12.

Comparative Example 3

[Synthesis of 2-(1-Methylheptyloxy)ethanol Using a Commercial Catalyst]

A reaction was conducted in a similar manner as in Example 3 except that, as a catalyst, a commercial alumina with 5 wt. % of palladium supported thereon (0.6 g) was used in place of the palladium catalyst (2). The weight ratio of monoalkyl ethers to dialkyl ethers was 25:75.

INDUSTRIAL APPLICABILITY

The palladium catalysts according to the present invention are excellent in reaction activity in the production of ethers, and provides monoethers with high selectivity in the synthesis of ethers by hydrogenolysis of cyclic acetals.

What is claimed is:

1. A process for the production of an ether, which comprises:

reacting a cyclic acetal containing at least one hydroxy group with hydrogen in the presence of a palladium catalyst supported on a mesoporous aluminosilicate whose pores are within the pore size range of 2 to 10 nm, said cyclic acetal having the structure of formula (1):

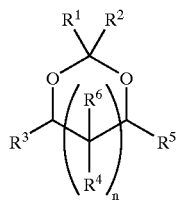
(1)

wherein $R^1$ and $R^2$ may be the same or different and each is hydrogen or a linear or branched hydrocarbon group having from 1 to 18 carbon atoms, $R^3$ is hydrogen, $R^5$ is a hydroxymethyl group and n is 0, or, alternatively, $R^3$ and $R^5$ are the same and each is hydrogen, n is 1, $R^4$ is hydrogen and $R^6$ is hydroxy, with the proviso that $R^1$ and $R^2$ are not both hydrogen at the same time, and each of $R^1$ and $R^2$, $R^3$ and $R^4$, and $R^3$ and $R^5$, together with the adjacent carbon atoms, may form a cyclic structure, said ether product having the formula (2)

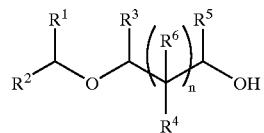
(2)

wherein $R^1$ to $R^6$ have the meanings indicated above.

2. The process according to claim 1, wherein said mesoporous aluminosilicate is treated with ammonia or a salt thereof.

3. The process according claim 1, wherein the palladium catalyst has a sodium content not greater than 0.1% by wt.

4. The process according to claim 2, wherein the palladium catalyst has a sodium content not greater than 0.1% by wt.

5. The process according to claim 1, wherein said cyclic acetal is a compound of formula (1) wherein $R^3$ is hydrogen, $R^5$ is a hydroxymethyl group and n is 0, or $R^3$ and $R^5$ are the same and each is hydrogen, n is 1, $R^4$ is hydrogen and $R^6$ is hydroxy.

* * * * *